United States Patent [19]

Garsky

[11] 4,305,852
[45] Dec. 15, 1981

[54] POLYPEPTIDE COMPOSITIONS

[75] Inventor: Victor M. Garsky, Radnor, Pa.

[73] Assignee: American Home Products Corporation, New York, N.Y.

[21] Appl. No.: 198,415

[22] Filed: Oct. 20, 1980

[51] Int. Cl.$^3$ .................... C08L 37/00; C07C 103/52
[52] U.S. Cl. .................... 260/8; 260/112.5 R
[58] Field of Search ............... 260/112.5 R, 8

[56] References Cited

U.S. PATENT DOCUMENTS 4,261,886  4/1981  Goldstein et al. ........... 260/112.5 R Primary Examiner—Delbert R. Phillips
Attorney, Agent, or Firm—George Tarnowski

[57] ABSTRACT

There are disclosed polypeptides having the formula:

R-Arg-Lys-Asp-Val-D-Ala-R$_1$ wherein

R is hydrogen, alkanoyl of 1–4 carbon atoms or aroyl of 6–10 carbon atoms; and

R$_1$ is amino, monoalkylamino of 1–4 carbon atoms, dialkylamino of 1–4 carbon atoms, hydroxy, alkoxy of 1–4 carbon atoms,

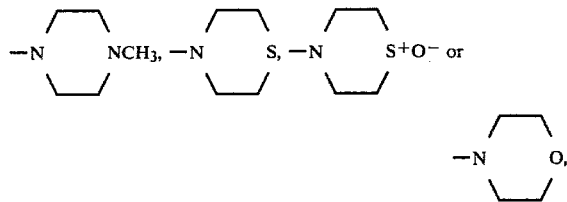

the fully protected peptide-resin intermediates thereof, or pharmaceutically acceptable salts thereof. These polypeptides have the capability of inducing the differentiation of t-lymphocytes and thus are useful in a number of therapeutic areas.

4 Claims, No Drawings

POLYPEPTIDE COMPOSITIONS

BACKGROUND OF THE INVENTION

Recent research has established the involvement of the thymus in the functioning of the immune system in mammalian species. It is in the thymus that haemopoietic stem cells become differentiated to mature immunocompetent lymphocytes called T-cells, which circulate to the blood, lymph, spleen and lymph nodes. The T-cells have immunological specificity and are involved in the cell-mediated immune responses, such as graft responses, response to viral infections, response to neoplasms and so forth. The body's response to antigenic material, such as for example in response to bacterial attack, is the province of antibody secreting cells, called B-cells, which are derived from bone marrow stem cells, but which are not differentiated in the thymus. The antibody response to an antigen, in many cases, requires the presence of appropriate T-cells, so that T-cells, and consequently the thymus, are necessary for the body's immune system to make not only cellular immunity responses, but also humoral antibody response. The thymic induction of the necessary differentiation of stem cells to T-cells is mediated by secretions of thymic hormones by the epithelial cells of the thymus.

The great interest in thymic substances, which may be implicated in various aspects of the immune response, has been instrumental in creating a very productive research effort. As a result of this research, a number of thymic substances have been reported in the literature. In the article by Goldstein and Maganaro in *Annals of the New York Academy of Sciences*, Volume 183, pps. 230-240, 1971, there are disclosures regarding the presence of a thymic polypeptide which causes a myasthenic neuromuscular block in animals, which is analogous to the human disease of myasthenia gravis. Further, in this article it was discovered that two distinct effects were caused by separate polypeptides in bovine thymus. One of these polypeptides, named "thymotoxin", was believed to cause myositis but it was further indicated that this polypeptide had not been isolated although it appeared to be a polypeptide of approximately 7,000 molecular weight, had a strong net positive charge and was retained on CM-Sephadex at a pH of 8.0.

In the publication "Nature", 247, 11, Jan. 4, 1975, there are described products identified as Thymin I and Thymin II which were found to be new polypeptides isolated from bovine thymus which have particular uses in various therapeutic areas. Because of the use of similar names for other products isolated from the thymus in the prior art, these Thymin I and Thymin II products are now named as Thymopoietin I and Thymopoietin II. These products and processes are described in U.S. Pat. No. 4,077,949. In U.S. Pat. No. 4,002,602 there are disclosed long chain polypeptides described as Ubiquitous Immunopoietic Polypeptides (UBIP), which polypeptide is a 74-amino acid polypeptide characterized by its ability to induce in vitro, in nanogram concentrations, the differentiation of both T-cell and B-cell immunocytes from precursors present in bone marrow or spleen. Thus, the polypeptide is useful in therapeutic areas involving thymic or immunity deficiencies and the like.

In U.S. Pat. No. 4,002,740 there are disclosed synthesized tridecapeptide compositions which have the capability of inducing the differentiation of T-lymphocytes but not of complement receptor B-lymphocytes. This polypeptide thus exhibited many of the characteristics of the long chain polypeptides isolated and named as thymopoietin in above-mentioned U.S. Pat. No. 4,077,949.

In U.S. Pat. No. 4,190,646, there are disclosed pentapeptides having the basic amino acid sequence:

R-NH-Arg-Lys-Asp-Val-Tyr-COR[1]

wherein R and R[1] are substituents which do not substantially affect the biological activity of the basic active sequence. In the publication "Science", 204, 1309 (1979), it is disclosed that this pentapeptide arginyl-lysyl-aspartyl-valyl-tyrosine corresponds to amino acid residues 32-36 in thymopoietin and that in vitro this pentapeptide induced the differentiation of murine prothymocytes to thymocytes and inhibited differentiative induction of cells of the B lineage, which is a combination of actions that is unique to the parent molecule thymopoietin. In vivo it displayed the further thymopoietin property of reducing the high numbers of autologous rosette-forming cells normally present in the spleens of athymic mice.

The present invention relates to novel polypeptides having the ability to induce differentiation of T-lymphocytes.

DESCRIPTION OF THE INVENTION

In accordance with this invention, there are provided pentapeptides having the structural formula:

R-Arg-Lys-Asp-Val-D-Ala-R$_1$ wherein
R is hydrogen, alkanoyl of 1-4 carbon atoms or aroyl of 6-10 carbon atoms; and
R$_1$ is amino, monoalkylamino of 1-4 carbon atoms, dialkylamino of 1-4 carbon atoms, hydroxy, alkoxy of 1-4 carbon atoms,

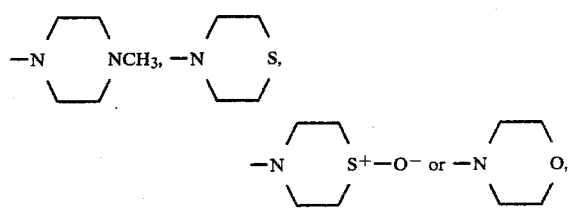

the fully protected peptide-resin intermediates thereof, or pharmaceutically acceptable salts thereof.

In the depicted formula and throughout the specification and claims, where the chirality of an amino acid is not indicated or otherwise stated, it is understood to be of the L-series.

The fully protected peptide-resin intermediates, which comprise an additional aspect of the invention, may be depicted as follows:

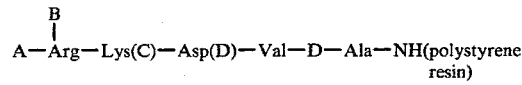

wherein A, B, C, and D are protecting groups which are hereinafter described. These intermediates comprise the fully protected pentapeptide bound to a benzhydrylamine polystyrene resin support employed in the solid phase synthesis of the polypeptide.

The pharmaceutically acceptable salts of the compounds of the invention are those non-toxic addition salts produced by known methods from acids conventionally employed with pharmaceuticals such as hydrochloric, hydrobromic, sulfuric, phosphoric, polyphosphoric, maleic, acetic, citric, benzoic, succinic, malonic, ascorbic or the like.

The peptides of the invention are able to directly induce the proliferation of T-cells in concentrations of about 1.5–100 ng/ml. The high activity of the compounds at such very low concentrations makes them useful in the therapeutical treatment of a number of disorders which involve the immune response. Of course, because the compounds perform certain of the thymic functions, they have application in various thymic function and immunity areas. A primary field of application is in the treatment of DiGeorge Syndrome, a condition in which there is a congenital absence of thymus. Injection of the polypeptides will overcome this deficiency. The polypeptides will increase or assist in therapeutic stimulation of cellular immunity and thereby become useful in the treatment of diseases involving chronic infection in vivo, such as fungal or mycoplasma infections, and the like. Further, the compounds are considered to be useful in any area in which cellular immunity is an issue and particularly where there are deficiencies in immunity such as in the DiGeorge Syndrome mentioned above. Also, where there is an excess of antibody production due to unbalanced T-cells and B-cells, the compounds can correct this condition by stimulating T-cell production. Thus, they may be of therapeutic use in certain auto-immune diseases in which damaging antibodies are present, for example, systemic lupus erythematosus. The polypeptides are also useful in inhibiting the uncontrolled proliferation of thymopoietin-responsive lymphocytes.

An important characteristic of the polypeptides is their in vivo ability to restore cells with the characteristic of the T-cells. Therefore, the polypeptides of this invention are active in many areas as a result of their ability to enhance the immune response in the body. Also, the peptides of this invention are highly active in very low concentrations ranging from 1.5 nanogram per ml., and are maximally active at concentrations from about 100 nanograms per ml. The carrier may be any of the well known carriers for this purpose including normal saline solutions, preferably with a protein diluent such as bovine serum albumin to prevent adsorptive losses to glassware at these low concentrations. For the treatment of DiGeorge Syndrome, the polypeptides may be administered at a rate of about 1.0 to 10 mg/kg of body weight. Generally, the same range of dosage amount may be used in treatment of the other conditions or diseases mentioned.

The polypeptides are produced by the well known solid phase method as described by Stewart et al., *Solid Phase Peptide Synthesis*, Freeman and Co., San Francisco, 1969. As applied to some of the compounds of this invention, α-amino protected D-alanine is attached to a benzhydrylamine polystyrene resin followed by removal of the α-amino protecting group with trifluoroacetic acid in methylene chloride, trifluoroacetic acid alone or HCl in dioxane. The deprotection is conducted at a temperature between about 0° C. and room temperature. Other standard cleaving reagents and conditions for removal of specific α-amino protecting groups may be used as described in Schroder E. Lubke, "The Peptides", 1, 72–75 (Academic Press, 1965). After removal of the α-amino protecting group the subsequent protected amino acids are coupled individually to the resin supported sequence, seriatim. Alternatively, small peptide fragments may be prepared by the solution method and introduced into the solid phase reactor in about a four fold excess. The coupling is carried out in dimethylformamide, methylene chloride, or a mixture of the two solvents. The success of each coupling reaction at each state of the synthesis is determined by the ninhydrin reaction as described by E. Kaiser et al., Analyt. Biochem., 34, 595 (1970). Where incomplete coupling has occurred, the reaction is repeated before the α-amino protecting group is removed for introduction of the next amino acid or amino acid sequence. The coupling reagent employed was diisopropylcarbodiimide.

After the desired amino acid sequence has been synthesized, the polypeptide is removed from the resin support by treatment with hydrogen fluoride and anisole to obtain the fully deprotected polypeptide. The polypeptide is then purified by gel filtration, high pressure preparative liquid chromatography and partition chromatography.

The ultimate fully protected, resin bound polypeptide of this invention specifically exemplified infra are $N^\alpha$-tert-butyloxycarbonyl-$N^g$-tosyl-L-arginyl-$N^\epsilon$-2-chlorobenzyloxycarbonyl-L-lysyl-$\beta$-benzyl-L-aspartyl-L-valyl-D-alanyl-benzhydrylamine polystyrene amide.

The protecting groups employed throughout the solid phase synthesis are well known to the art. The α-amino protecting groups employed with each amino acid introduced in sequence of the ultimate polypeptide are of the (1) acyl type protecting groups illustrated by the following: formyl, trifluoroacetyl, phthalyl, p-toluenesulfonyl (tosyl), nitrophenylsulfenyl, etc.; (2) aromatic urethane type protecting groups illustrated by benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxybenzyloxycarbonyl; (3) aliphatic urethane protecting groups illustrated by tert-butyloxycarbonyl, diisopropylmethoxycarbonyl, isopropyloxycarbonyl, allyloxycarbonyl, 2,2,2-trichloroethoxycarbonyl, amyloxycarbonyl; (4) cycloalkyl urethane type protecting groups illustrated by cyclopentyloxycarbonyl, adamantyloxycarbonyl, cyclohexyloxycarbonyl; (5) thiourethane type protecting groups as illustrated by triphenylmethyl (trityl); (7) trialkylsilane groups such as trimethylsilane. The preferred α-amino protecting group is tert-butyloxycarbonyl.

Protection for the side chain amino group of amino acids such as lysine, may be by tosyl, t-amyloxycarbonyl, t-butyloxycarbonyl, diisopropyloxycarbonyl, benzyloxycarbonyl, halobenzyloxycarbonyl, nitrobenzyloxycarbonyl, and the like, the 2-chlorobenzyloxycarbonyl group being preferred.

Protection for the side chain carboxyl group of amino acids such as aspartic acid, may be by any ester of anhydride which is not removed during removal of the α-amino protecting group. Preferably the benzyl ester is employed to protect the carboxy group.

In selecting a particular side-chain protecting group to be used in the synthesis of the peptides of this invention, the following rules should be followed: (a) the side-chain protecting group must be stable to the reagent and under the restriction conditions selected for removing the α-amino protecting group at each step of the synthesis, (b) the protecting group must retain its protecting properties (i.e. not be split off under coupling conditions), and (c) the side-chain protecting group must be removable upon the completion of the synthesis containing the desired amino acid sequence under reaction conditions that will not alter the peptide chain. The substituted pentapeptide wherein the terminal amino acid groups may be further substituted can be prepared by reaction of this basic pentapeptide with suitable reagents to prepare the desired derivatives. Reactions of this type such as acylation, esterification, amidation and the like, are of course well known in the art.

The following examples illustrate the preparation of L-arginyl-L-lysyl-L-aspartyl-L-valyl-D-alanyl-amide triacetate, which is representative, in its solid phase preparation and biological activity, of the other compounds within the scope of the invention.

EXAMPLE 1

$N^\alpha$-tert-Butyloxycarbonyl-$N^g$-tosyl-L-arginyl-$N^\epsilon$-2-chlorobenzyloxycarbonyl-L-lysyl-$\beta$-benzyl-L-aspartyl-L-valyl-D-alanyl-benzhydrylamine polystyrene amide To a 200 ml reaction vessel is added 7.0 g. of benzhydrylamine resin (5.6 moles free amine content). The resin is then treated in the following manner:
1. methylene chloride (three times).
2. 5 minute prewash with 30% trifluoroacetic acid-methylene chloride (v/v) containing 0.5% dithioerythritol.
3. 25 minute treatment with the above described trifluoroacetic acid.
4. methylene chloride (three times).
5. 10 minute treatment with triethylamine-dimethylformamide 15% (v/v).
6. dimethylformamide (three times).
7. methylene chloride (three times).

A contact time of 2 minutes is allowed for each wash unless otherwise indicated.

The resin is gently stirred with t-Boc-D-alanine and 1-hydroxy-benzotriazole (HOBT) in 50% methylene chloride-dimethylformamide (14 moles t-Boc-D-alanine and 15 moles HOBT). Following the addition of the above reagents the mixture is treated with 15 mM of diisopropylcarbodiimide (the DIC is added in two equal portions over 30 minutes). After stirring overnight the peptide-resin is washed successively with dimethylformamide (twice), 12% triethylamine-dimethylformamide (once) and methylene chloride (thrice). To test for completeness of reaction the peptide-resin is subjected to a ninhydrin color test following the procedure of E. Kaiser et al., Analytical Biochemistry 34, 595, (1970).

The deprotection of the attached amino acid is carried out as described in steps (2) through (7) above.

The following amino acid residues are introduced consecutively: t-BOC-Val (14 moles, 15 moles HOBT and 15 moles DIC), t-Boc-$\beta$-Bzl-Asp (14 moles, 15 moles HOBT and 15 moles DIC), t-Boc-Cl-Z-Lys (14 moles, 15 moles HOBT and 15 moles DIC), t-Boc-$N^g$-Tos-Arg (14 moles, 15 moles HOBT and 15 moles DIC). The washed pentapeptide resin is dried in vacuo.

EXAMPLE 2

L-arginyl-L-lysyl-L-aspartyl-L-valyl-D-alaninamide triacetate

The pentapeptide resin of Example 1 is treated in vacuo with anhydrous liquid hydrogen fluoride (200 ml) and anisole (20 ml) at 0° for 1 hour. The hydrogen fluoride and anisole are removed under reduced pressure and the residue treated with AG-3-X4A ion exchange resin (acetate form) for 30 minutes, filtered and lyophilized to give a yield of 1.11 g.

The above titled crude product is purified as follows: 1.11 g. of material is dissolved in a minimum amount of 2 N acetic acid and applied to a column (2.5×200 cm) of Sephadex G-10 in 2 N acetic acid. The column is eluted with 2 N acetic acid and 13 ml fractions collected. The column effluent is monitored at 254 nm. Fractions 35–41 are combined, concentrated and further purified by applying the material in a small volume of upper phase B:A:P, 5:11:3 (n-butanol:0.1% acetic acid:pyridine) onto a column (2.5×100 cm) of Sephadex G-25 medium previously equilibrated with lower phase of the above system and then upper phase. The column is eluted with upper phase B:A:P and 13 ml fractions collected. Tubes 47–77 are shown to be homogeneous by thin layer chromatography. Thin layer chromatograms, are visualized with ninhydrin and chlorine peptide reagent.

Amino acid analysis following methane sulfonic acid hydrolysis gives the following ratios: Ala 1.00; Val 1.07; Lys 1.02; Arg 1.02; Asp 1.06. TLC data: $R_f$=0.17 in 4:1:1:2 (n-butanol-acetic acid-pyridine-water) on silica plates. $R_f$=0.40 in 4:1:1:2 on cellulose plates. Analysis of the product by high pressure liquid chromatography on a $\mu$ Bondapak $C_{18}$ column (97% 0.1 M ammonium acetate: 3% acetonitrile, pH 4.0) shows the product to be 98% pure.

EXAMPLE 3

The activity of the compound of Example 2 is determined according to the following procedure:

T lymphocytes are isolated from spleens of male CBA/J or NZB mice. Cell homogenates are prepared in Hank's balanced salt solution (HBSS). After removal of larger particles and repeated washing of the cells in HBSS they are suspended in minimum essential medium (MEM) and passed through a glass wool column to remove macrophages. The cells are then incubated on a nylon wool column at 37° C., 95% air, 5% $CO_2$, for 45 minutes. The non-adherant T lymphocytes are then eluted from the column, counted, and adjusted to 20×10$^6$ cells/ml. 50 $\mu$l of cells are cultured (37° C., 95% air, 5% $CO_2$) with compound, for 48 hours before the addition of 0.5 $\mu$Ci. of 3H-thymidine for the last 16 hours of culture. The total volume of the culture system is 200 $\mu$l. The cells are then harvested on a multiple automatic sample harvester (Mash II), the glass fiber filter disks placed in 10 ml. of xylene base scintillation fluid, and counted for 1 minute in a liquid scintillation counter. Results are reported as CPM±SE. The findings are summarized in Table 1.

TABLE 1

| Compound | Concentration $\mu$g/culture | CPM ± SE | p |
|---|---|---|---|
| Arg—Lys—Asp—Val—D—Ala—$NH_2$ | 0.0015 | 20305 ± 2347 | <0.02 |
|  | 0.006 | 18640 ± 1830 | <0.01 |
|  | 0.025 | 30181 ± 3895 | <0.01 |
|  | 0.1 | 21887 ± 3143 | <0.02 |
| Blank | — | 9876 ± 951 |  |
| Arg—Lys—Asp—Val—D—Ala—$NH_2$ | 0.00075 | 18983 ± 2651 | N.S. |
|  | 0.0015 | 22966 ± 562 | <0.1 |
|  | 0.006 | 28559 ± 3663 | <0.05 |
|  | 0.025 | 25515 ± 2486 | <0.05 |
| Blank | — | 19275 ± 1298 |  |

The results show that the peptides of the invention have marked activity in stimulating the proliferation of T-cells at very low concentration levels.

What is claimed is:

1. A polypeptide having the following formula:

R-Arg-Lys-Asp-Val-D-Ala-R$_1$ wherein

R is hydrogen, alkanoyl of 1–4 carbon atoms or aroyl of 6–10 carbon atoms; and

R$_1$ is amino, monoalkylamino of 1–4 carbon atoms, dialkylamino of 1–4 carbon atoms, hydroxy, alkoxy of 1–4 carbon atoms, $$-N\underset{\diagdown\diagup}{\diagup\diagdown}NCH_3, -N\underset{\diagdown\diagup}{\diagup\diagdown}S, -N\underset{\diagdown\diagup}{\diagup\diagdown}S^+O^- \text{ or}$$

$$-N\underset{\diagdown\diagup}{\diagup\diagdown}O,$$

the fully protected peptide-resin intermediates thereof, or pharmaceutically acceptable salts thereof.

2. The compound of claim 1, which is Arg-Lys-Asp-Val-D-Ala-NH$_2$ or a pharmaceutically acceptable salt thereof.

3. A compound of the formula:

$$\overset{B}{\underset{|}{A-Arg-Lys(C)-Asp(D)-Val-D-Ala-NH}}(\text{polystyrene resin})$$

wherein

A is an α-amino protecting group;

B is a protecting group for the guanyl group of arginine;

C is an amino protecting group; and

D is a protecting group for the side chain carboxy group of aspartic acid.

4. The compound of claim 5 wherein:

A is t-butyloxycarbonyl;

B is tosyl;

C is 2-chlorobenzyloxycarbonyl; and

D is benzyl.

* * * * *